(12) United States Patent
Duchamp et al.

(10) Patent No.: US 7,837,035 B2
(45) Date of Patent: Nov. 23, 2010

(54) PACKAGING DEVICE FOR MEDICAL APPARATUS

(75) Inventors: Jacques Duchamp, Bron (FR); Michel Neyton, Villeurbanne (FR); Patrick Paule, Lyons (FR); Frederic Tenant, Villeurbanne (FR); Guillaume Vernin, Meyzieu (FR)

(73) Assignee: Gambro Lundia AB, Lund (SE)

( * ) Notice: Subject to any disclaimer, the term of this patent is extended or adjusted under 35 U.S.C. 154(b) by 161 days.

(21) Appl. No.: 11/814,354

(22) PCT Filed: Jul. 18, 2005

(86) PCT No.: PCT/IB2005/002033

§ 371 (c)(1),
(2), (4) Date: Jul. 19, 2007

(87) PCT Pub. No.: WO2006/077457

PCT Pub. Date: Jul. 27, 2006

(65) Prior Publication Data

US 2008/0093246 A1    Apr. 24, 2008

(30) Foreign Application Priority Data

Jan. 21, 2005   (FR) .................................. 05 00629

(51) Int. Cl.
*A61B 17/06* (2006.01)
*A61B 19/02* (2006.01)

(52) U.S. Cl. .................... 206/438; 206/571; 206/305; 206/364; 604/4.01; 604/6.09; 604/6.11; 210/646; 229/240

(58) Field of Classification Search ................. 206/438, 206/570, 571, 572, 305, 364; 229/200, 220, 229/240; 604/4.01, 6.09, 6.11; 210/645, 210/646

See application file for complete search history.

(56) References Cited

U.S. PATENT DOCUMENTS

| 4,173,655 | A |   | 11/1979 | Capo |
| 4,173,655 | A |   | 11/1979 | Capo |
| D268,649 | S | * | 4/1983 | Adamson et al. ............. D9/416 |
| 4,479,760 | A |   | 10/1984 | Bilstad et al. |
| 4,479,761 | A | * | 10/1984 | Bilstad et al. ................ 417/395 |
| 4,479,762 | A | * | 10/1984 | Bilstad et al. ................ 417/395 |
| 4,596,696 | A | * | 6/1986 | Scoville, Jr. .................. 422/61 |
| 5,441,636 | A |   | 8/1995 | Chevallet et al. |
| 5,895,571 | A |   | 4/1999 | Utterberg |
| 6,189,780 | B1 | * | 2/2001 | Kanter ....................... 229/242 |
| 6,811,749 | B2 |   | 11/2004 | Lindsay |

(Continued)

FOREIGN PATENT DOCUMENTS

DE   1118094 B   11/1961

(Continued)

*Primary Examiner*—Mickey Yu
*Assistant Examiner*—Chun Cheung
(74) *Attorney, Agent, or Firm*—Pearne & Gordon LLP

(57) ABSTRACT

The invention relates to a disposable packaging device (1) including a wall (2) for accommodating a medical article (100) for use in conjunction with a medical machine (200), the medical article (100) including mounting means (101), the medical machine (200) including mounting means (201) for engagement with the mounting means of the medical article (101), the packaging device including:—a passage opening (20) defined in the wall (2) and having a configuration such that the mounting means (101) of the packaged article can be engaged with the mounting means of the machine (201);—a preferential rupture zone (30) produced on the wall 2 to allow predetermined rupture of the wall (2).

48 Claims, 6 Drawing Sheets

Invention                    Invention

U.S. PATENT DOCUMENTS

| | | |
|---|---|---|
| 6,913,189 B2 * | 7/2005 | Oliff et al. ............ 229/120.011 |
| 7,374,043 B2 * | 5/2008 | Holley et al. ................. 206/427 |
| 2002/0134827 A1 * | 9/2002 | Sinclair et al. .............. 229/240 |
| 2003/0029763 A1 | 2/2003 | Reif et al. |
| 2004/0167457 A1 | 8/2004 | Tonelli et al. |

FOREIGN PATENT DOCUMENTS

| | | |
|---|---|---|
| DE | 9419884 U1 | 2/1995 |
| FR | 1357126 A | 4/1964 |
| JP | 05317418 A | 12/1993 |
| JP | 3001561 | 6/1994 |
| JP | 06292722 A | 10/1994 |
| JP | 08098881 A | 4/1996 |
| JP | 08187285 A | 7/1996 |
| JP | 2006263000 A | 10/2006 |
| JP | 2006523469 T | 10/2006 |
| WO | 2004069299 A2 | 8/2004 |

* cited by examiner

Invention FIG 3

Invention  FIG 4

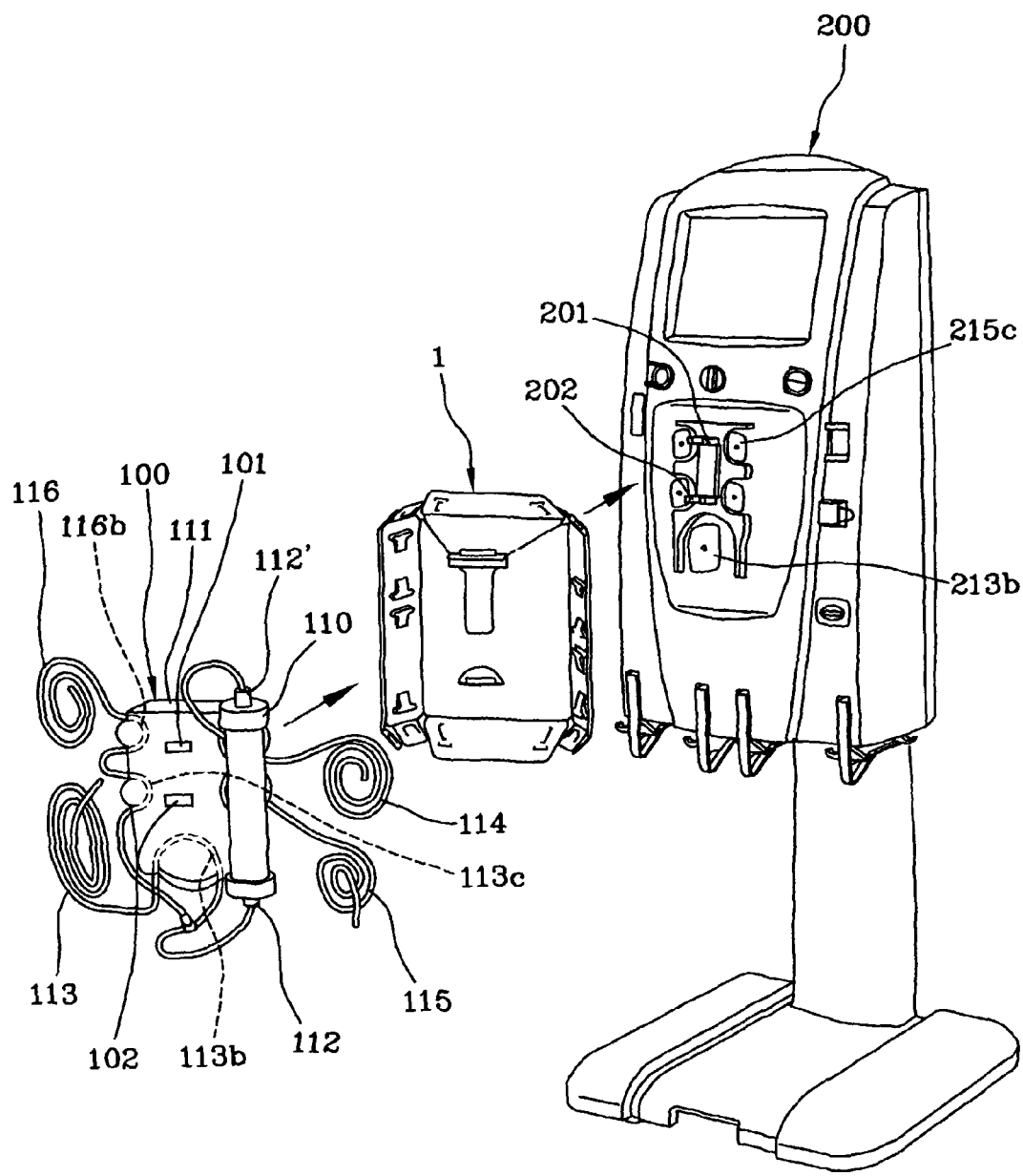
Invention FIG 6

PACKAGING DEVICE FOR MEDICAL APPARATUS

TECHNICAL FIELD OF THE INVENTION

The present invention relates to a packaging device for packaging a medical article designed to be used in conjunction with a medical machine onto which it will be installed before use.

More particularly, the invention may be applied in the medical field of extracorporeal blood treatment, for example dialysis. Extracorporeal blood treatment requires a dialysis treatment machine and the use, in conjunction with the machine, of disposable medical articles that are installed on the machine before the start of the treatment session and are removed from the machine at the end of the session and then thrown away.

PRIOR ART

The applicant currently makes use of a packaging device for a medical article as illustrated in FIGS. 1 and 2. This packaging device includes a wall 2 for receiving the medical article 100. The medical article may be at least one dialyser 110, or, alternatively, a set of pre installed disposable elements that will work in conjunction with one another, which will be connected up to the medical machine (cf., in FIG. 6, the illustration of the medical machine 200). The applicant uses, for example, as medical article, a moulded plastic element (111—called a "cassette") that serves as a support and onto which at least one dialyser 110 is premounted. The dialyser 110 is a box including a membrane delimiting a first compartment for the passage of blood and a second compartment for the passage of waste liquid and including, therefore, access points (112, 112') such as one or two entries and two exits over which are mounted plastic lines (113, 114, 115, 116) that are designed to be connected to the hydraulic circuit of the dialysis machine. The cassette 111 holds the access points (112, 112') of the dialyser and includes eyelets for receiving and holding plastic lines (113, 114, 115, 116) over each of the access points (112, 112'), in particular. The cassette 111 also includes preformed cavities (101, 102) for engagement with members of the medical machine such as fixing means (hooks). The plastic lines (113, 114, 115, 116) may have a preformed U shaped configuration in order to be positioned in order to cooperate with pumps of the medical machine. The medical article may thus be composed of several elements and requires a packaging that includes a wall that receives and maintains these elements without risk of damage to the elements during storage or during transportation prior to use of the medical article, and without risk of the elements becoming disconnected from one another when the article is an assembly of several parts.

The known packaging device used has the form of a rectangular box having a rear panel 51 and four lateral panels (52, 53, 54, 55), and includes holding elements (60, 61, 62, 63, 64, 65) for receiving and holding the medical article, such as, for example, slots in the panels of the box for forming lugs that will be, inserted into cavities in the article.

It has been observed that this packaging device is perfectly suitable on the one hand for protecting the article it contains from any stress prior to use (e.g. protecting from impacts caused during transportation, stresses upon assembly or during any sterilization) and on the other holding the various elements of the medical article in position during storage and transportation. Thus, medical staff, when needing to use an article of this type, will go through the following successive steps:

finding the packaged article in the clinic's storage area;
removing the packaging from the medical article in the treatment room;
taking out the medical article;
throwing away the packaging;
installing the article on the medical machine and going through the steps of coupling each required element of the article to the corresponding elements of the machine (e.g. connecting the plastic lines of the article over the access points to the pipes of the hydraulic circuit of the medical machine), and starting up initialization of the machine.

However, the following drawbacks have been observed in connection with installing the article:

during the step of removing the packaging from the article, staff still need to place the packaged article on a preferably flat work surface in order to correctly open the packaging without disconnecting elements of the article or damaging the medical article. This step takes a certain amount of time and requires a flat surface in the treatment room. This is a drawback in any type of treatment and, more particularly, if the patient is one undergoing intensive care for whom dialysis treatment is required suddenly and has to be applied as rapidly as possible. The time spent on set up is particularly regrettable, since intensive care staff are less accustomed to this type of machine than staff who deal with chronic dialysis treatment on a daily basis;

furthermore, the medical article may be installed on the machine incorrectly. The medical article includes lines that are, for packaging purposes, each rolled up on themselves and held by a tie. When the packaging is removed from the medical article, these lines, or any other similar element not rigidly connected to the cassette, are no longer held in position, and when the cassette of the medical article is picked up by the operator the lines simply hang in space and the operator himself has to attempt to hold them during installation of the article. If one of the lines is not securely held by the user, it may become trapped behind the part of the article that is to be placed against the machine. The line is then immobilized, flattened and even cut, and the medical article has to be reinstalled or, worse, is no longer useable.

As regards correct installation, patent application US2003/0029763 relates to a disposable sterile filter that is designed to be coupled to a syringe. The sterile filter is encapsulated on its own in a sealed package. The package consists of a box and a lid formed from a sheet sealed over the box and capable of being penetrated at a point axially in line with the filter. In order not to contaminate the filter when coupling it to a syringe, the packaging sheet has preformed rupture lines along which the sheet, subject to an appropriate force, ruptures in order to allow the filter to be picked up by the syringe coupled to it without it being necessary in a first stage to remove the filter from its packaging.

The installation method includes the following successive steps: pushing the end of a syringe through one point in the packaging sheet, firmly fitting the syringe into the filter, moving the filter/syringe assembly in the direction of the removal of the filter from the packaging, and tearing the sheet along pre cut lines. Installation takes place without the sterile filter being touched.

This patent application teaches the use of the packaging for installing a syringe on a filter, the particular feature of which is the sterility of the filter that is to be preserved during storage and during coupling. Thus, the packaging must be sealed and must allow full coupling of the two elements by means of simultaneous insertion of the syringe through the sheet.

Furthermore, patent application U.S. Pat. No. 6,811,749 relates to an assembly/package that includes disposable components of an extracorporeal circuit for cardiac bypass surgery that are designed to be connected up to a corresponding medical machine. The assembly contains a plurality of components separated by holding panels and grouped into subassemblies packaged by means of a cover sheet. The assembly may be packaged in a sealed pouch that includes all the disposable devices and the panels for keeping them sterile. The assembly may, without distinction, be attached to or detached from a support device of the machine without the pouch being removed. The pouch may be made in two pieces joined together by a sealing strip that joins them and seals the pouch. The sealed pouch is used to preserve the sterility of the package and may, without distinction, be detached prior to or after assembly of the device and the machine.

SUMMARY OF THE INVENTION

On the basis of the packaging it uses itself, the applicant attempted to resolve these drawbacks arising from use of the medical article. The problem posed is that of allowing correct, rapid and easy installation of a medical article on a medical machine designed to interact with the article.

In order to solve this problem, provision is made, according to the invention, for a disposable packaging device 1 including:
- a wall 2 for accommodating a medical article 100 for use in conjunction with a medical machine 200, the medical article 100 including mounting means 101, the medical machine 200 including mounting means 201 for engagement with the mounting means of the medical article 101;
- a passage opening 20 defined in the wall 2 and having a configuration such that the mounting means 101 of the packaged article can be engaged with the mounting means of the machine 201;
- a preferential rupture zone 30 produced on the wall 2 to allow predetermined rupture of the wall 2.

The invention also relates to the disposable packaging device 1 defined above that includes a medical article 100 designed to be used in conjunction with a medical machine 200, the medical article including mounting means 100 designed for engagement with mounting means 201 of the machine, the medical article 100 being packaged such that the passage opening 20 allows the mounting means 101 of the article to be engaged with the mounting means 201 of the machine.

Lastly, the invention relates to a method for mounting a medical article 100 packaged by a disposable packaging device 1 on a medical machine 200;
- the article 100 including mounting means 101;
- the machine 200 including mounting means 201 designed for engagement with the article mounting means 101;
- the packaging device 1 including:
  - a wall 2 for receiving the article 100 and having a configuration such that it allows the mounting means 101 of the packaged article 100 to be engaged with the machine mounting means 201;
  - a preferential rupture zone 30 produced on the wall 2 to allow a predetermined rupture of the wall 2;

the method including the steps of:
a) taking the article 100 packaged by the packaging device 1;
b) engaging the article mounting means 101 with the machine mounting means 201 through the passage opening; then
c) disengaging the packaging device of the article by rupturing the preferential rupture zone 30 in the manner predetermined by this zone.

The invention makes it possible to solve the problem posed for the following reasons:
- the passage opening 20 defined in the wall 2 of the packaging device 1 makes it possible to install at least a part of the medical article 100 on the medical machine 200 while the article 100 is still packaged. There is no longer a need for a flat surface on which to place the packaged article 100 in order to remove it from its packaging 1. The facilitated installation process includes one less stage and requires one less use constraint (work surface);
- furthermore, the article 100 is installed while the elements constituting the article are held in place: hence no line or similar element not securely fixed to the base of the article can be wedged or damaged during installation and the medical article is engaged correctly on the medical machine;
- in addition, the preferential rupture zone makes it possible to detach the packaging device once it has been coupled to the medical machine by means of preferential rupture of this zone in a predetermined manner. The packaging is removed from the article without damaging or removing any element of the article.

Other advantages and characteristics of the invention will become apparent on reading the following description.

BRIEF DESCRIPTION OF THE DRAWINGS

Reference will be made to the appended drawings, in which:

FIG. 6 shows an exploded perspective view of the set up consisting of the medical article 100 and the packaging device 1 according to the invention installed on the medical machine 200.

FIG. 3 shows a disposable packaging device 1 according to the invention that, in addition to the characteristics of the invention that will be described below, may include the characteristics of the packaging device according to the prior art illustrated in FIG. 1 for receiving the article illustrated in FIG. 2. Shared characteristics are denoted by the same numerals.

Figure 1:
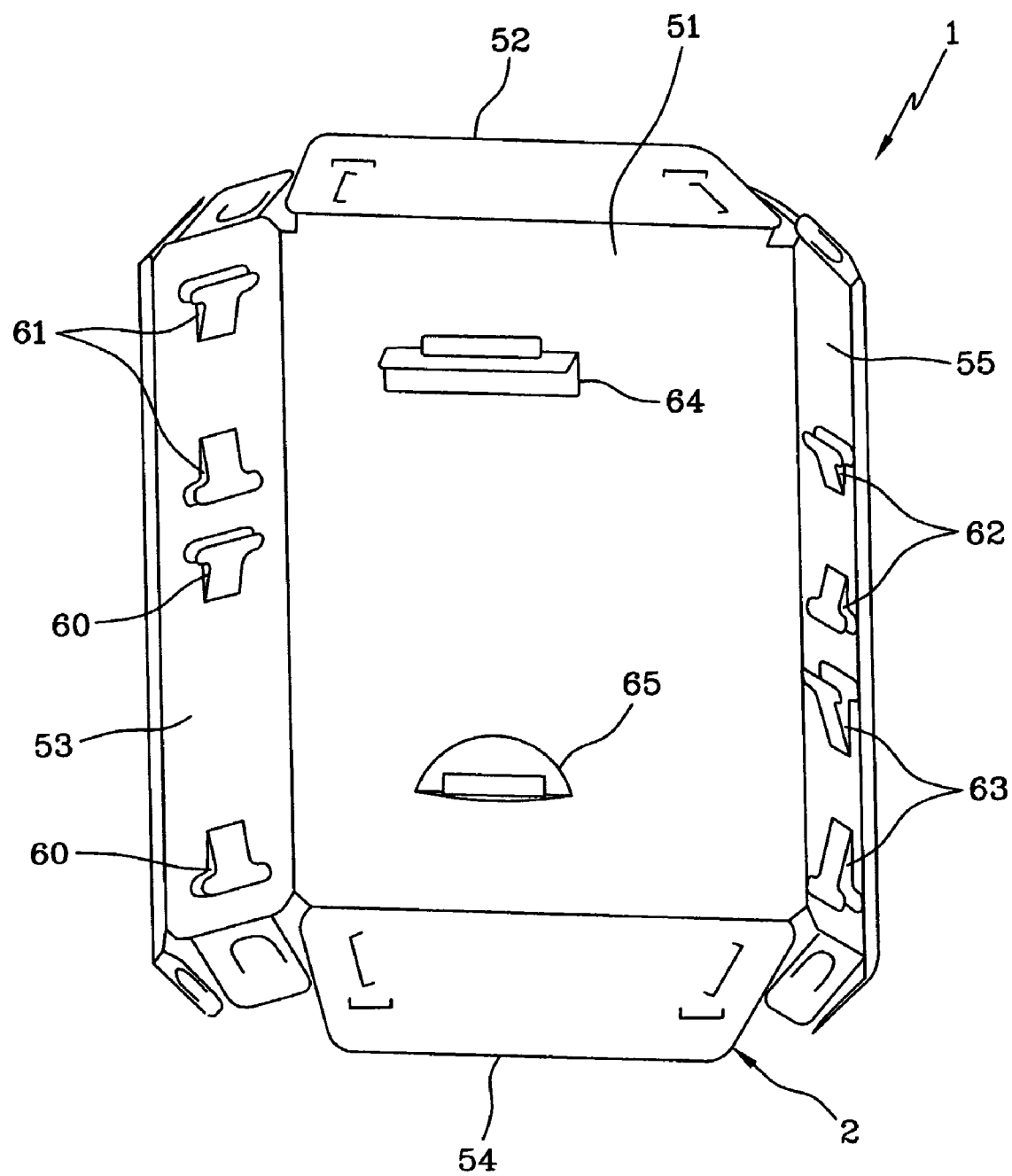
FIG. 1 shows the packaging 1 alone without the medical article according to the prior art in a perspective view in a partially open position.
Figure 2:
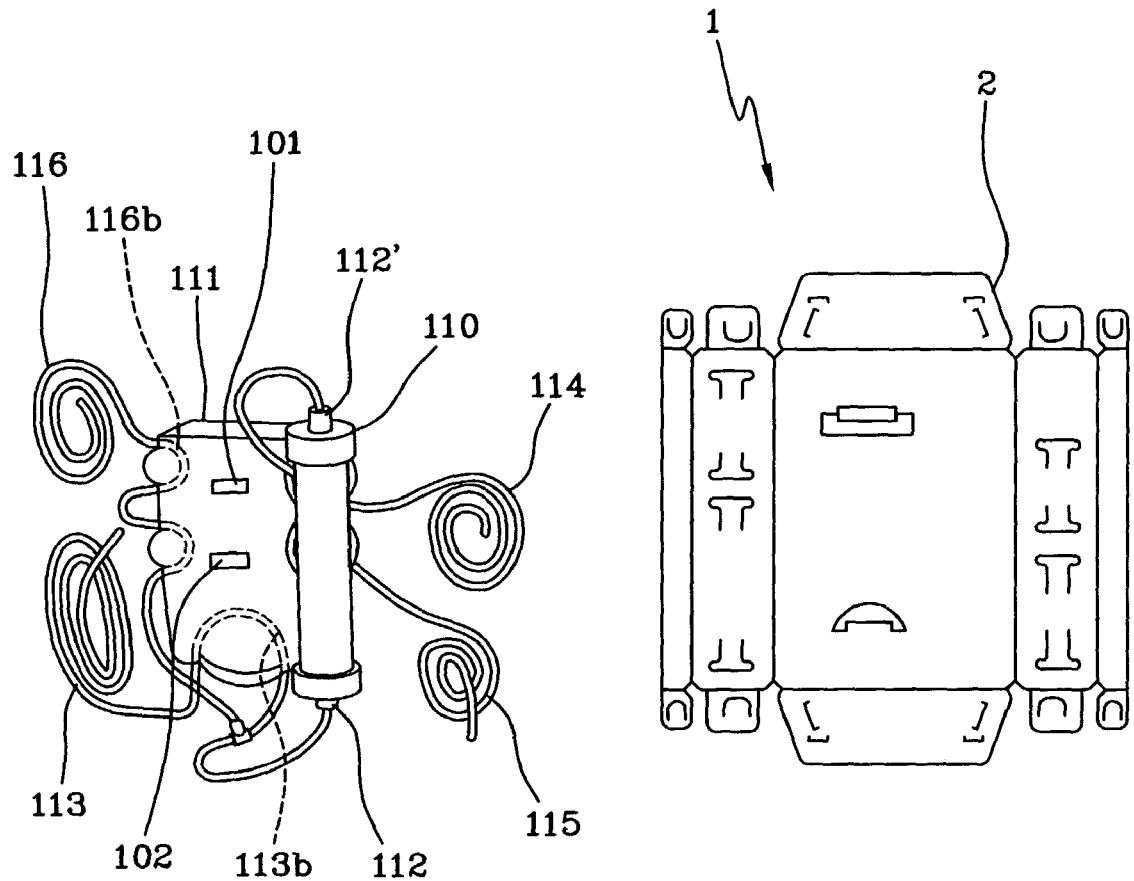
FIG. 2 shows the packaging 1 according to the prior art in front view in an entirely open position and ready to receive the medical article 100.
Figure 3:
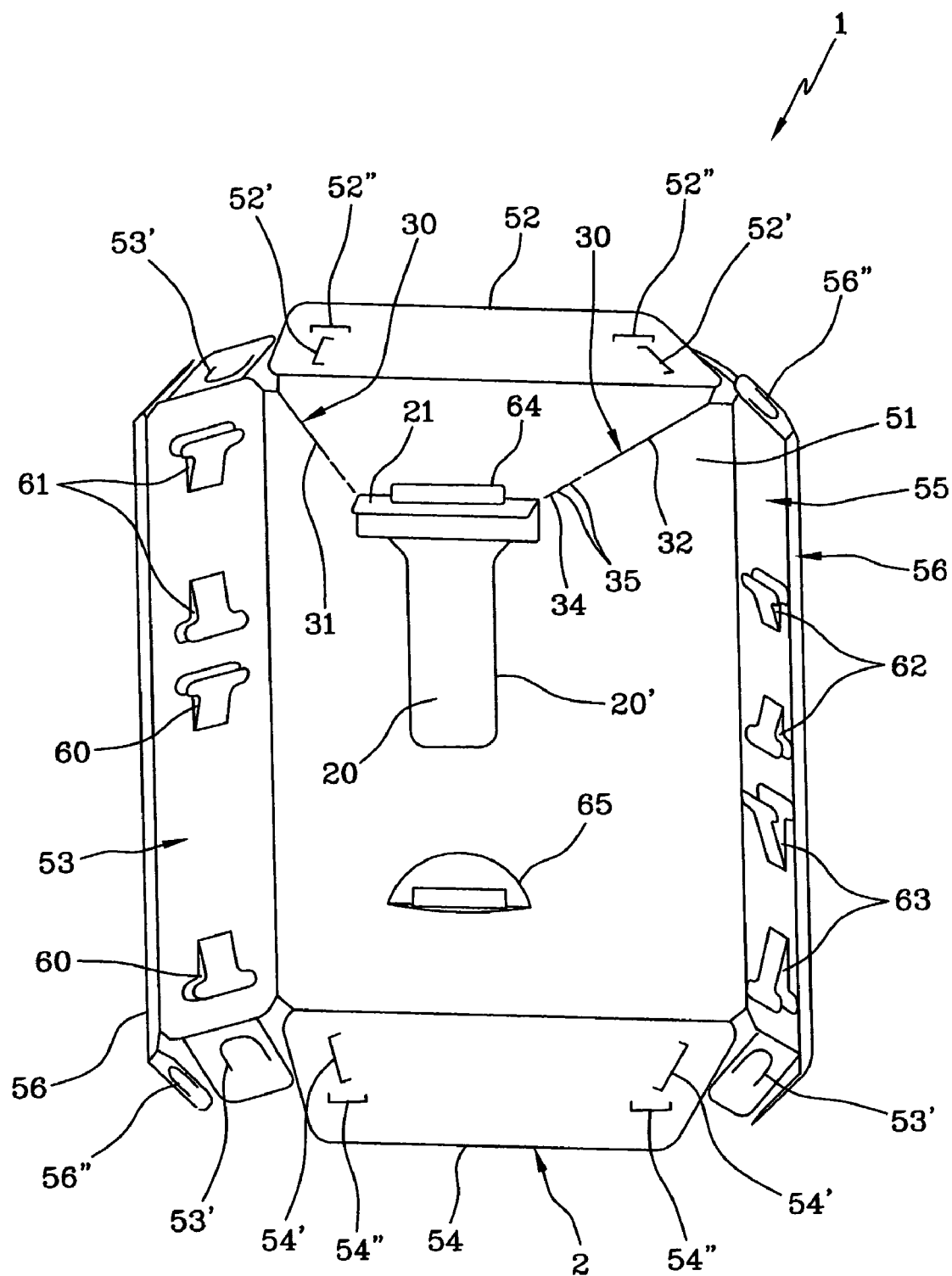
FIGS. 3 and 4, respectively, show the packaging device 1 alone according to the invention without the medical article in perspective view in a partially open position and entirely closed position, respectively.

The packaging device 1 of FIG. 3 includes a wall 2 for accommodating a medical article 100 that is designed for use in conjunction with a medical machine 200, the medical article 100 including mounting means 101 and the medical machine 200 including mounting means 201 designed for engagement with the mounting means 101 of the medical article. The device 1 also includes a passage opening 20 defined in the wall 2 with a configuration such that the mounting means 101 of the packaged article can be engaged with the mounting means 201 of the machine, and a preferential rupture zone 30 produced on the wall 2 in order to allow predetermined rupture of the wall 2.

Details on the Nature of the Preferential Rupture Zone:

The preferential rupture zone 30 may include a structural weakness produced on the wall 2. In this case, the structural weakness includes a structural discontinuity comprising at least one element chosen from the group that includes an incision in the wall 2, a cut through the wall 2, a series of holes in the wall 2, a fold in the wall 2, a change of thickness in the wall 2 or a change of material in the wall 2.

When the discontinuity comprises a change of material, the change of material includes a material having a lower strength than that of the wall 2.

These various structural weaknesses or weaknesses of material may, alone or in combination, form the preferential rupture zone 30 of the wall. This is chosen, in particular, as a function of the shape of the zone, which depends on the shape of the packaging, the article and the machine.

The part of the preferential rupture zone 30 includes a non uniform structural weakness.

Figure 4:
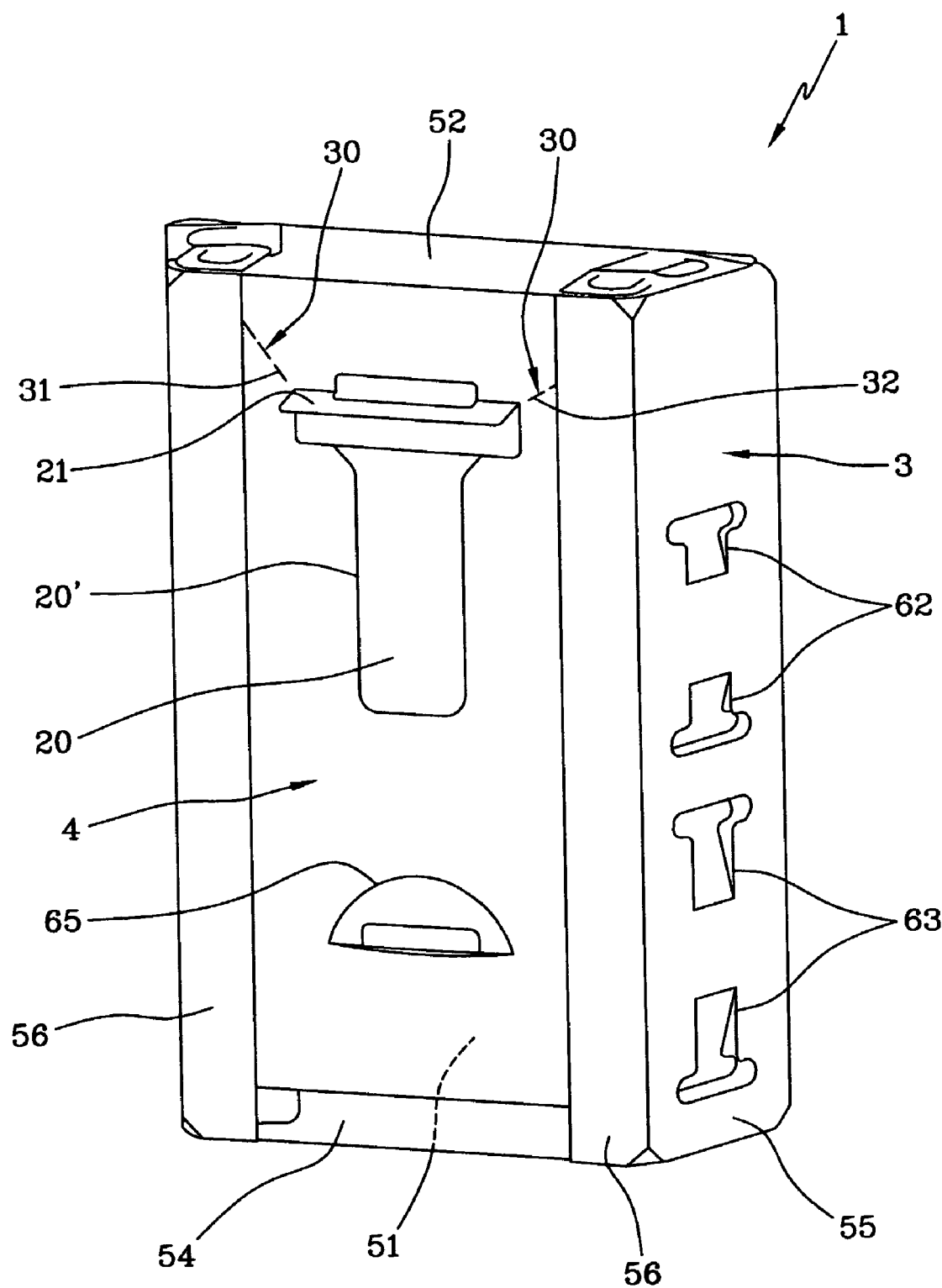
Figure 5:
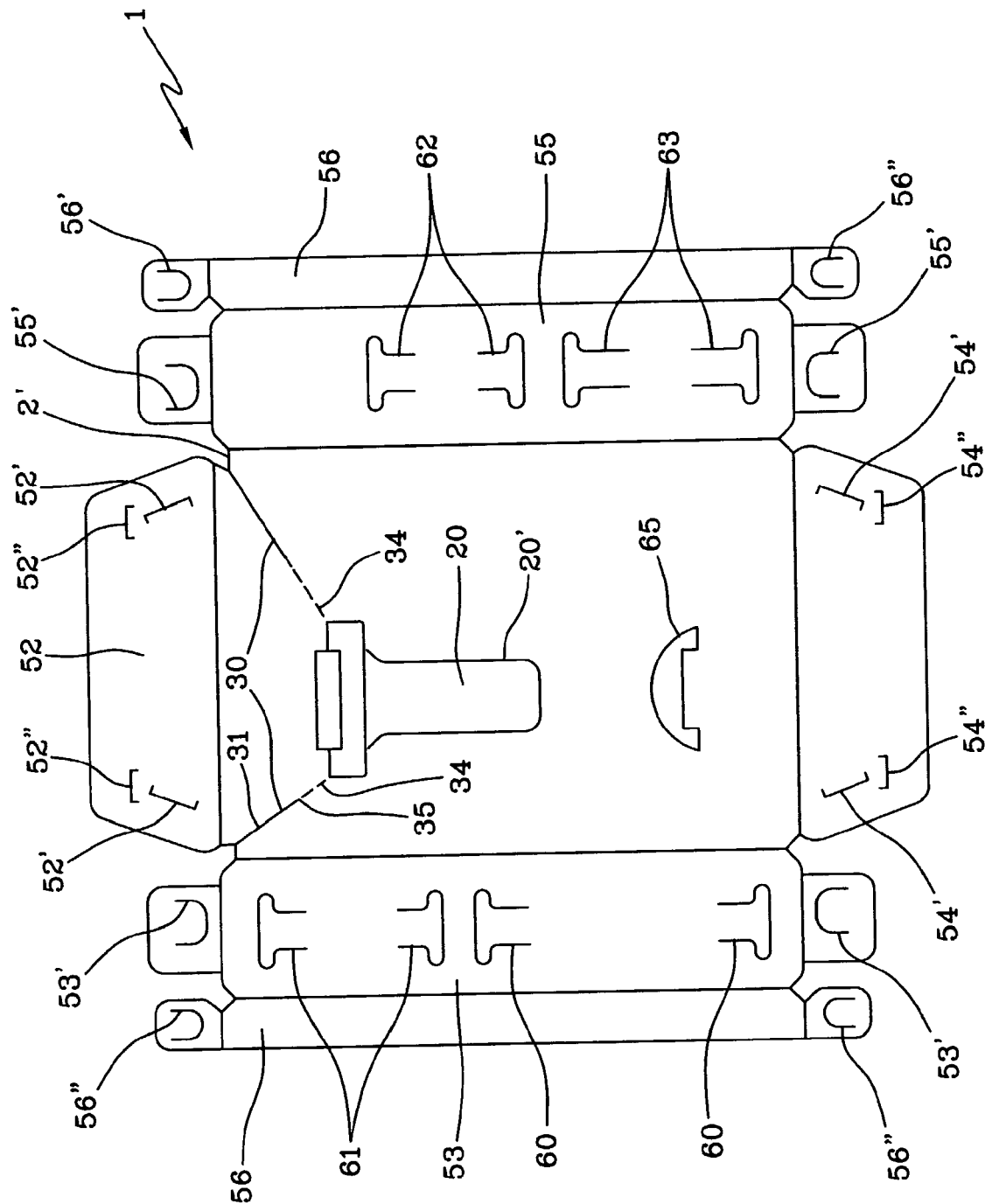
FIG. 5 shows a front view of the packaging device 1 alone according to the invention in the open position.

Details on the Form of the Wall:

The wall 2 of the packaging device may include a rear panel 51 on which the passage opening 20 is defined. The wall 2 may define a box whose rear panel 51 is a polygon and which has as many lateral panels (52, 53, 54, 55) as the polygon has sides. The rear panel 51 may be substantially rectangular. The box may include a front panel 56 designed to at least partially cover the medical article 100. For example, and as illustrated in FIGS. 3, 4 and 5, this front panel 56 is formed from two parts that partially cover the box over two opposite sides of the rear panel 51. However, a front panel 56 that entirely covers the box may be produced for forming a box that is practically sealed, with the exception of the passage opening 20.

At least two panels chosen from among the lateral panels (52, 53, 54, 55) and the rear panel 51 may be formed from a sheet. "Sheet" is understood to mean a surface of which two dimensions are much larger than the third dimension (the thickness).

This sheet may be rigid or semi rigid. "Rigid sheet" is understood to mean a sheet that does not flex under bending stresses and does not deform under deformation stresses. "Semi rigid sheet" is understood to mean a sheet that will flex or roll up under a bending stress and that will not deform under deformation stresses, by means of pulling, for example.

The material may, more particularly, have good compliance: when it is subject to pressures, it then returns to its initial position. All the lateral panels (52, 53, 54, 55) may be formed from a plastic sheet, e.g. a polypropylene sheet, or from a sheet of cardboard, etc.

In order to simplify the construction of the packaging device, for example, the rear panel 51, the panels (52, 53, 54, 55) and the front panel 56 may be formed from a single sheet folded so as to form the panels.

Each lateral panel (52, 53, 54, 55) may be connected to each of its adjacent lateral panels by an attachment means (52', 53', 54', 55') formed on each panel (52, 53, 54, 55). At least one lateral panel attachment means (52', 53', 54', 55') comprises at least one cut defining a slot (52', 54') on a panel and at least one cut defining a lug (53', 55') on a panel designed for engagement in the slot (52', 54') of the corresponding adjacent lateral panel.

When the wall defines a front panel 56, the front panel 56 may include attachment means 56" designed to be connected to attachment means (52", 54") of at least one of the lateral panels (52, 54). At least one attachment means of the lateral panels (52, 54) may comprise at least one cut defining a slot (52", 54") on the lateral panel (52, 54) designed to receive at least one cut defining a lug (56") on the front panel (56).

The wall may also be provided with attachment means (64, 65) for the medical article. These means for attachment to the article may be slots made in the wall 2 for receiving and holding parts of the medical article or for engaging in cavities of the medical article, or may be lugs (62, 63) for receiving, for example, lines of the medical article wound up on themselves. These slots or lugs may be positioned on any front, rear or lateral panel. Any known holding means may be envisaged and positioned at any suitable place so as to interact with at least one part of the chosen article.

Specific Details on the Material of the Wall:

The wall may include a semi rigid part 3. "Semi rigid" is understood to mean a material that will flex or roll up under a bending stress and that will not deform under deformation stresses, for example by means of pulling.

Such a material may be a plastic (polypropylene, for example), capable of bending slightly under the stress but not deforming, or cardboard.

The semi rigid part 3 may at least partially delimit the passage opening 20 and may also totally delimit the passage opening 20.

Similarly, the wall 2 may include a plastic film 4, alone or in combination with a semi rigid part 3. "Film" is understood to mean a thin sheet capable of matching the shapes of the medical article. It may be a plastic film (for example, polyethylene), which is heat formable and would be placed on or around the article and heated in order to match the shapes of the article and hold each element of the article. The description "blister" is generally used.

When the wall of the packaging device is made from a plastic film 4 and from a semi rigid part 3, the plastic film 4 may partially cover the semi rigid part 3 and surround the passage opening 20. This may take the form of a rigid or semi rigid box covered by a plastic film, the film being fixed by heat welding or adhesive bonding. Alternatively, the film 4 may totally cover the semi rigid part 3 and surround the passage opening 20. This film 4 may be fixed to the semi rigid part 3, for example by means of heat sealing or adhesive bonding, and the film includes a part outside the fixing (a tab, for example), that the operator can pull in order to remove the film. The preferential rupture zone may thus extend over the semi rigid part 3 or over the film 4, or over both (3, 4).

Furthermore, a part of the wall may be transparent in order to identify the medical article. A part of the wall may receive words describing the product and its characteristics.

Specific Details on the Geometry of the Preferential Rupture Zone:

The passage opening 20 is delimited by a contour 20'. The rupture zone 30 may extend from at least one point of this contour 20'. The preferential rupture zone 30 may therefore have a non uniform structural weakness that is greater in the zone close to the contour 20' of the passage opening 20.

The wall 2 may include a gripping zone 21 partially delimited by at least one point of the contour 20' of the passage opening 20. Once the packaged article has been coupled to the machine by at least one mounting means, the operator may rupture the wall along its preferential rupture zone by seizing and pulling on the gripping zone 21. The gripping zone 21 may be delimited by a part of the wall (rear panel 51, for example) that is cut and extends transversely relative to this part of the wall in order to form a kind of tab to be seized. The gripping zone may also be a protuberance formed in the wall and capable of being seized by an operator. The gripping zone may even have the dual function of possibly being gripped by an operator and holding a part of the medical article.

The wall may thus delimit a receptacle for the article, the only opening of which is the passage opening 20 delimiting a single contour 20'. Alternatively, the wall 2 may be delimited by an auxiliary contour 2'. This means that, in addition to the contour 20' defining the passage opening, the wall has an auxiliary contour 2' and will thus not be closed entirely (except for the passage opening 20 that is still present). In this case, the preferential rupture zone 30 may extend between at least one point of the contour 20' and at least one point of the auxiliary contour 2' in order to allow a predetermined rupture between the two contours. Hence, the non uniform structural weakness of the rupture zone 30 is greater in the zone close to the auxiliary contour 2' of the wall 2: this makes it possible more easily to initiate rupture of the zone starting from the point of the auxiliary contour 2'.

In a particular manner, the preferential rupture zone 30 may include at least one rupture line 31. This line may also have a narrow width (less than a few millimeters). This zone may also have the form of two lines of identical width offset from one another by a short distance (a few millimeters).

In the case of a rupture line 31, this may be a straight line segment.

The preferential rupture zone 30 may also include at least one auxiliary rupture line 32. Similarly, the auxiliary line 32 may be a straight line segment.

At least one of these rupture lines (31, 32) is defined by a discontinuous cut 33 formed on the wall 2. This cut may be an incision in the material of the wall or a cut traversing the wall.

This discontinuous cut 33 may include a plurality of consecutive cut segments 34, the width of which may be non uniform. More particularly, over at least one portion of the discontinuous cut 33 the length of the cut segments 34 increases or, alternatively, decreases, as it approaches the contour 20' of the passage opening 20. This absence of uniformity is fixed as a function of the chosen tear direction.

When the wall is pulled via a gripping point close to the contour 20' of the passage opening 20, the rupture is initiated more easily by the relatively long length of cut segments close to the contour 20'. This may apply in reverse when gripping takes place close to the auxiliary contour 2'. Furthermore, the discontinuous cut 33 may at least partially define non cut segments 35, the length of which increases or decreases from the contour 2' towards the auxiliary contour 20' of the passage opening 20.

Moreover, at least one of the straight line segments (31, 32) may be chosen so as substantially to define the smallest length connecting a point of the contour 20' of the passage opening 20 at a point of the auxiliary contour 2' of the wall 2. As illustrated in FIG. 3, the segments 31 and 32 are positioned such that the length of the segment is the shortest distance between a point of the contour 2' and a point of the contour 20'.

The straight line segments (31, 32) may be substantially perpendicular and thus define two parts of the wall of different surface areas: a part having a small surface area and another having a larger surface area. Alternatively, the straight line segments (31, 32) may be substantially parallel, for example on the same straight line, more particularly on a straight line included in a transverse symmetrical plane of the packaging device.

Method for Manufacturing the Packaging Device:

The packaging device 1 may be manufactured as follows: a semi rigid polypropylene sheet is formed. Its contour is cut to produce a rectangular rear panel, four lateral panels and two portions constituting a partial front panel 56. At the same time, or after the contour is cut, on the one hand the cutting of slots takes place in each part used as a panel (51, 52, 53, 54, 55), to form means of attachment to other panels (52', 52", 53', 54', 54", 55', 56', 56"), and, on the other hand, the cutting of slots or of openings takes place in the rear panel, in particular in order to form holding means (65, 64) for the medical article or slots (30, 61, 62, 63) in lateral panels (53, 55).

Simultaneously, or after cutting of the contour, formation of the preferential rupture zone 30 also takes place, by means of cutting, incision or formation of holes. It should be noted that, as an alternative, the rupture zone 30 may be formed during manufacture of the wall if the zone is a weakness of material or a difference in thickness. Alternatively, also, formation of the preferential rupture zone 30 may take place after cutting of the wall if this zone 30 is the result of folding.

Simultaneously, or after cutting the contour, formation of the passage opening 20 in the wall takes place. This may be the result of cutting, for example.

Specific Details on the Method of Assembling the Article with the Packaging Device:

The method for assembling the medical article 100 with the packaging device 1 may include the following steps:

- the slots (64, 65) in the rear panel are bent slightly in order to receive the parts of the corresponding medical article or in order to form gripping zones;
- the medical article 100 is placed on the wall 2 of the packaging device 1;
- certain parts of the article (for example plastic lines) are inserted into the lugs (60, 61, 62, 63) of the lateral panels (53, 55) and cavities of the article are inserted in slots or openings (65, 64) of the wall 2.
  - Next, the lateral panels (52, 53, 54, 55) are folded and attached together by the corresponding attachment means (52', 53', 54', 55') and the two parts of the front panel are attached by the corresponding attachment means (52", 54", 56") in order to form a box that will hold the medical article.

The disposable packaging device 1 described above will include a medical article 100 designed to be used in conjunction with a medical machine 200, the medical article 100 including mounting means 101 designed for engagement with mounting means 201 of the machine 200. The medical article 100 will be packaged such that the passage opening 20 allows the article mounting means 101 to be engaged with the machine mounting means 201.

More particularly, the article mounting means 101 define at least one cavity 102 and the machine mounting means 201 define at least one protuberance 202 capable of passing through the passage opening 20 in order to be engaged in the cavity 102.

More precisely, the medical article includes the following elements:

- a treatment unit 110 that includes a semi permeable membrane delimiting a first compartment for the passage of blood and a second compartment for the passage of waste liquid;
- a blood circuit that includes an entry line 113 connected at a first access point 112 to the blood compartment and an exit line 114 connected at a second access point 112' to the blood compartment;

a waste liquid circuit with at least one exit line 115 connected at least a first access point to the waste liquid compartment;

a support unit 111 on which the following are fixed:
 a. the treatment unit 110;
 b. at least two points of a line of the blood circuit in order to form a U (113b) to enable said line to be coupled with a peristaltic pump (213b) of the medical machine;
 c. at least two points of the waste liquid-circuit line 115 in order to form a U to enable said line to be coupled with a pump (215c) of the medical machine.

It should be pointed out that that which is called the "passage opening" may, in particular, be a single hole, but a person skilled in the art may adapt this passage opening in order to make it several holes traversing the packaging, depending on the mounting means of the machine and of the article. Thus, the packaging device may include as many passage openings 20 as there are machine protuberances necessary for mounting the article, or, alternatively, may include at least one opening of which the contour makes it possible to receive the several protuberances of the machine. In FIG. 6, the medical article includes two cavities (101, 102), into each of which a pair of hooks (201, 202) of the machine will be fixed, obviously in a removable manner.

Method for Installing the Packaged Article on the Medical Machine:

The method for mounting the medical article 100 packaged by the disposable packaging device 1 onto the medical machine 200 uses:

the medical article 100 that includes mounting means 101;

the medical machine 200 that includes mounting means 201 designed for engagement with the article mounting means 101;

the packaging device 1 including:
 a wall 2 for receiving the medical article 100;
 a passage opening 20 defined in the wall 2 and having a configuration such that it enables the mounting means 101 of the packaged article to be engaged with the machine mounting means 201;
 a preferential rupture zone 30 produced on the wall 2 to allow predetermined rupture of the wall 2.

This method includes the steps of:
a) taking the medical article 100 packaged by the packaging device 1;
b) engaging the article mounting means 101 with the machine mounting means 201 through the passage opening 20; then
c) disengaging the packaging device of the article by rupturing the preferential rupture zone 30 in the manner predetermined by this zone.

The disengagement step may include two successive substeps:
c') rupturing the preferential rupture zone 30 in the manner predetermined by this zone;
c") removing the packaging device 1 of the article 100 whose preferential zone is ruptured.

If the passage opening 20 is delimited by a contour 20' and if the rupture zone 30 extends from at least a point of the contour 20' along at least one rupture line 31, then:
 the rupture step includes the tearing of the wall 2 at least along the rupture line 31; and
 the removal step includes pulling via two gripping points of the torn wall.

If the passage opening 20 delimits a contour 20', the wall 2 delimits an auxiliary contour 2' and if the rupture zone 30 includes at least two rupture lines (31, 32) each extending between a point of the contour 20' and a point of the auxiliary contour 2', then:
 the rupture step includes the tearing of the wall 2 along each rupture line (31, 32) in order to form two parts of the wall;
 the removal step includes the removal of a first part of the torn wall by pulling via at least one gripping point and the removal of the other part of the torn wall by means of pulling via at least one gripping point.

When the wall 2 includes a sheet 3 in which are formed a rear panel 51, lateral panels (52, 53, 54, 55) each having an attachment means (52', 53', 54', 55') for connecting each lateral panel to each of its two adjacent lateral panels, then the removal step includes the detachment of the attachment means (52', 53', 54', 55') connecting each lateral panel (52, 53, 54, 55) to an adjacent lateral panel. The step of detaching the attachment means (52', 53', 54', 55') of the lateral panels may precede the rupture step.

When the wall includes a front panel 56, the detachment step may first include detachment of the attachment means (52", 54", 56") between the front panel and the lateral panels in question and then mutual detachment of the lateral panels.

More particularly, the step of detaching all the attachment means (52', 52", 53', 54', 54", 55', 56") precedes the step of rupturing the zone.

After removal of the packaging device 1, the article mounting means 101 may be engaged in an operational position with the machine mounting means 201. In fact, mounting may include two steps: premounting of the article mounting means on the machine mounting means and a subsequent step of mounting the same means in an operational position.

The invention affords numerous advantages. It makes it possible:
 to install at least one part of the medical article 100 on the medical machine 200 whilst the article 100 is still packaged;
 to avoid the use of a work surface for receiving the packaged article 100 in order to remove it from its packaging 1;
 to save time during installation of the medical article onto the machine;
 to avoid an element of the medical article being installed incorrectly on the machine;
 to prevent an element of the medical article being damaged during installation on the machine by said element being held in the packaging device during installation.

The invention claimed is:

1. Disposable packaging device (1) including:
a medical article (100) adapted to be used in conjunction with a medical machine (200), the medical article (100) including mounting means (101) adapted to be engaged with mounting means (201) of the machine (200);
a wall (2) accommodating said medical article (100);
a passage opening (20) defined in the wall (2), said passage opening having a closed perimeter, said passage opening being located and having a configuration such that the mounting means (101) of the packaged medical article can be engaged, through the passage opening (20), with the mounting means of the machine (201) while the medical article (100) is still packaged in the wall (2) of the disposable packaging device (1); and
a preferential rupture zone (30) provided on the wall (2) to allow predetermined rupture of the wall (2) and being effective to guide predetermined rupture of the wall (2) up to and through the closed perimeter of the passage opening.

2. Device according to claim 1 in which the preferential rupture zone (30) includes a structural weakness produced on the wall (2).

3. Device according to claim 2 in which the structural weakness includes a structural discontinuity comprising at least one element chosen from the group including:
   a. an incision in the wall (2);
   b. a cut through the wall (2);
   c. a series of holes in the wall (2);
   d. a fold in the wall (2);
   e. a change of thickness in the wall (2);
   f. a change of material in the wall (2).

4. Device according to claim 3 in which the change of material includes a material having a lower strength than that of the wall (2).

5. Device according to claim 1 in which a part of the preferential rupture zone (30) includes a non uniform structural weakness.

6. Device according to claim 1 in which the wall (2) includes a rear panel (51) on which the passage opening (20) is defined.

7. Device according to claim 6 in which the wall (2) defines a box whose rear panel (51) is a polygon and which includes as many lateral panels (52, 53, 54, 55) as there are sides of the polygon.

8. Device according to claim 7 in which the rear panel (51) is substantially rectangular.

9. Device according to claim 6 including a front panel (56) for at least partially covering the medical article (100).

10. Device according to claim 7 in which at least two panels chosen from the lateral panels (52, 53, 54, 55) and the rear panel (51) are formed from a sheet.

11. Device according to claim 10 in which at least the rear panel (51) and at least two lateral panels (52, 53, 54, 55) are formed from a single folded sheet.

12. Device according to claim 10 comprising four lateral panels and in which the rear panel (51) is substantially rectangular, and in which the rear panel (51), the four lateral panels (52, 53, 54, 55) and a front panel (56) are formed from a single folded sheet.

13. Device according to claim 11 in which each lateral panel (52, 53, 54, 55) is designed to be connected to each of its adjacent lateral panels (52, 53, 54, 55) by an attachment means (52', 53', 54', 55') formed at least on each lateral panel (52, 53, 54, 55).

14. Device according to claim 13 in which at least one attachment means (52', 53', 54', 55') of the lateral panels comprises at least one cut defining a slot (52', 54') on a panel and at least one cut defining a lug (53', 55') on a panel for engagement in the slot (52', 54') of the corresponding adjacent lateral panel.

15. Device according to claim 13 further comprising a front panel (56) which includes attachment means (56") designed to be connected to attachment means (52", 54") of at least one of the lateral panels (52, 54).

16. Device according to claim 15 in which at least one attachment means of the lateral panels (52, 54) comprises at least one cut defining a slot (52", 54") on the lateral panel (52, 54) designed to receive at least one cut defining a lug (56"') on the front panel (56).

17. Device according to claim 1 in which the wall includes a semi rigid part (3).

18. Device according to claim 17 in which the semi rigid part (3) at least partially delimits the passage opening (20).

19. Device according to claim 18 in which the semi rigid part totally delimits the passage opening (20).

20. Device according to claim 1 in which the wall (2) includes a plastic film (4).

21. Device according to claim 17 in which the wall (2) includes a plastic film (4) partially covering the semi rigid part (3) and surrounding the passage opening (20).

22. Device according to claim 17 in which the wall (2) includes a plastic film (4) totally covering the semi rigid part (3) and surrounding the passage opening (20).

23. Device according to claim 1 in which the passage opening (20) is delimited by a contour (20') and the rupture zone (30) extends from at least one point of this contour (20').

24. Device according to claim 5 in which the passage opening (20) is delimited by a contour (20') and the rupture zone (30) extends from at least one point of this contour (20') and the non uniform structural weakness is greater in the zone close to the contour (20') of the passage opening (20).

25. Device according to claim 23 in which the wall (2) includes a gripping zone (21) partially delimited by at least one point of the contour (20') of the passage opening (20).

26. Device according to claim 25 in which the wall includes a rear panel (51) and the gripping zone (21) extends transversely relative to the rear panel (51).

27. Device according to claim 23 in which the wall (2) is delimited by an auxiliary contour (2') and in which the preferential rupture zone (30) extends between at least one point of the contour (20') and at least one point of the auxiliary contour (2').

28. Device according to claim 27 in which a part of the preferential rupture zone (30) includes a non uniform structural weakness and the non uniform structural weakness is greater in the zone close to the auxiliary contour (2') of the wall (2).

29. Device according to claim 23 in which the preferential rupture zone (30) includes a rupture line (31).

30. Device according to claim 29 in which the rupture line (31) is a straight line segment.

31. Device according to claim 29 in which the preferential rupture zone (30) includes at least one auxiliary rupture line (32).

32. Device according to claim 31 in which the auxiliary line (32) is a straight line segment.

33. Device according to claim 29 in which at least one of the rupture lines (31, 32) is defined by a discontinuous cut (33) formed through the wall (2).

34. Device according to claim 33 in which the discontinuous cut (33) comprises a plurality of consecutive cut segments (34).

35. Device according to claim 34 in which the cut segments (34) have a non uniform length.

36. Device according to claim 35 in which, over at least a portion of the discontinuous cut (33), the length of the cut segments (34) increases in the direction of the contour (20') of the passage opening (20).

37. Device according to claim 35 in which, over at least a portion of the discontinuous cut (33), the length of the cut segments (34) decreases in the direction of the contour (20') of the passage opening (20).

38. Device according to claim 23 in which the preferential rupture zone (30) includes a rupture line (31) being a straight line segment and includes at least one auxiliary rupture line (32) being a straight line segment, and in which at least one of the straight line segments (31, 32) defines substantially the smallest length connecting a point of the contour (20) of the passage opening (2') to a point of the auxiliary contour (2') of the wall (2).

39. Device according to claim 23 in which the preferential rupture zone (30) includes a rupture line (31) being a straight line segment and includes at least one auxiliary rupture line (32) being a straight line segment, and in which the straight line segments (31, 32) are substantially perpendicular.

40. Device according to claim 23 in which the preferential rupture zone (30) includes a rupture line (31) being a straight line segment and includes at least one auxiliary rupture line (32) being a straight line segment, and in which the straight line segments (31, 32) are substantially parallel.

41. Device according to claim 1 in which the article mounting means (101) define at least one cavity (102) and the machine mounting means (201) define at least one protuberance (202) capable of passing through the passage opening (20) for engagement in the cavity (102).

42. Device according to claim 1 in which the article (100) includes the following elements:
- a treatment unit (110) including a semi permeable membrane delimiting a first compartment for the passage of blood and a second compartment for the passage of waste liquid;
- a blood circuit including an entry line (113) connected to a first access (112) to the blood compartment and an exit line (114) connected to a second access (112') to the blood compartment;
- a waste liquid circuit with at least one exit line (115) connected to at least a first access to the waste liquid compartment;
- a support unit (111) on which the following are fixed:
  - a. the treatment unit (110);
  - b. at least two points of a line of the blood circuit in order to form a U (113b) to allow said line to be coupled to a peristaltic pump (213b) of the medical machine;
  - c. at least two points of the waste liquid circuit line (115) in order to form a U to allow said line to be coupled to a pump (215c) of the medical machine;

the support unit (111) including at least one cavity (101, 102) for receiving at least one protuberance (201, 202) of the medical machine (200).

43. Method for mounting on a medical machine (200) a medical article (100) packaged as part of a disposable packaging device (1),
the method comprising the steps of:
a) providing a disposable packaging device according to claim 1;
b) engaging the article mounting means (101) with the machine mounting means (201) through the passage opening (20); then
c) rupturing the preferential rupture zone (30) in a manner predetermined by said zone.

44. Method according to claim 43, further comprising, after said rupturing step, a step of disengaging at least a portion of said wall from said medical article.

45. Method according to claim 44 in which the passage opening (20) is delimited by a contour (20') and the rupture zone (30) extends from at least one point of the contour (20') along at least one rupture line (31), wherein:
- the rupturing step includes a tearing of the wall (2) at least along the rupture line (31); and
- the disengaging step includes pulling via two gripping points of the torn wall.

46. Method according to claim 44 in which the passage opening (20) delimits a contour (20'), the wall (2) delimits an auxiliary contour (2') and the rupture zone (30) includes at least two rupture lines (31, 32) each extending between a point of the contour (20') and a point of the auxiliary contour (2'), wherein:
- the rupturing step includes a tearing of the wall (2) along each rupture line (31, 32) in order to form two parts of the wall;
- the disengaging step includes the removal of a first part of the torn wall by pulling via at least one gripping point and the removal of the other part of the torn wall by means of pulling via at least one gripping point.

47. Method according to claim 44 in which the wall (2) includes a sheet from which the following are formed:
- a rear panel (51);
- lateral panels (52, 53, 54, 55) each having an attachment means (52', 53', 54', 55') for connecting each lateral panel to each of its two adjacent lateral panels;
  - and in which the disengaging step includes the detachment of the attachment means (52', 53', 54', 55') connecting each lateral panel (52, 53, 54, 55) to an adjacent lateral panel.

48. Method according to claim 47 in which the step of detachment of the attachment means (52', 53', 54', 55') of the lateral panels precedes the rupturing step.

* * * * *